United States Patent [19]

Keränen et al.

[11] Patent Number: 5,473,438
[45] Date of Patent: Dec. 5, 1995

[54] SPECTROSCOPIC METHOD AND APPARATUS FOR MEASURING OPTICAL RADIATION

[75] Inventors: Heimo Keränen; Pasi Pietarinen, both of Oulu; Tapani Alajärvi, Tornio; Veli Väli, Kiiminki, all of Finland

[73] Assignee: Rautaruukki Oy, Oulu, Finland

[21] Appl. No.: 295,809

[22] PCT Filed: Mar. 19, 1993

[86] PCT No.: PCT/FI93/00104

§ 371 Date: Sep. 2, 1994

§ 102(e) Date: Sep. 2, 1994

[87] PCT Pub. No.: WO93/19350

PCT Pub. Date: Sep. 30, 1993

[30] Foreign Application Priority Data

Mar. 20, 1992 [FI] Finland ................ 921221

[51] Int. Cl.$^6$ ................... G01J 3/51
[52] U.S. Cl. ................... 356/419; 359/220
[58] Field of Search ................ 356/402, 418, 356/419; 359/220, 226

[56] References Cited

U.S. PATENT DOCUMENTS

| | | |
|---|---|---|
| 3,523,734 | 8/1970 | Brehm et al. |
| 3,667,850 | 6/1972 | Smith et al. ............ 359/220 X |
| 3,797,908 | 3/1974 | Ward et al. ............ 359/220 X |
| 4,099,051 | 7/1978 | Gugliotta ............ 250/236 |
| 4,687,329 | 8/1987 | Schultz ............ 356/328 |
| 4,748,329 | 5/1988 | Cielo et al. ............ 250/560 |
| 4,923,263 | 5/1990 | Johnson . |
| 5,050,991 | 9/1991 | Welch ............ 356/326 |
| 5,089,908 | 2/1992 | Jodoin et al. ............ 359/212 |

FOREIGN PATENT DOCUMENTS

WO9007697 7/1990 WIPO.

OTHER PUBLICATIONS

Patent Abstracts of Japan, vol. 9, No. 281, p. 403, abstracts of JP A 60-123742.
Patent Abstracts of Japan, vol. 12, No. 76, p. 675, abstracts of JP A 62-215229.

Primary Examiner—Vincent P. McGraw
Attorney, Agent, or Firm—Sughrue, Mion, Zinn, Macpeak and Seas

[57] ABSTRACT

The intensity 2 of radiation coming from an object 1 to be measured and illuminated by collimated radiation is measured at several wavelengths by focusing the radiation, via a lens 4 and a planar mirror 6, on a detector group 3 having several detector elements (3a to 3d). The radiation coming from the object is directed by the lens and the mirror such that, by rotating the mirror, tilted at a small angle with respect to its axis 5, around this axis and by keeping the radiation on the surface of the mirror, the focus F of radiation is moved in a detector plane D along an uninterrupted circular path R crossing each detector element positioned substantially in the same plane and excited at a different wavelength.

10 Claims, 2 Drawing Sheets

SPECTROSCOPIC METHOD AND APPARATUS FOR MEASURING OPTICAL RADIATION

BACKGROUND OF THE INVENTION

The invention relates to a method of measuring optical radiation, in which method the intensity of a radiation coming from an object to be measured and to be lighted by collimated radiation is measured at several wavelengths by focusing the radiation by an optical means and a mirror means on a detector group comprising several detector elements.

Spectroscopic measurements are based on an investigation of a spectrum of radiation coming from an object to be measured. It depends on the properties of the object to be measured how the spectral distribution of the radiation, which is reflected or emitted from the object or which has penetrated the object, is within a frequency range. For instance, the thickness of a film of slushing oil or impurities on the surface of the object influences the distribution and amplitude of the spectrum reflected from the object or, in practice, from the film on the surface.

Typical of spectroscopic measurements is that the radiation obtained from a spot-like light source is collimated, i.e. made parallel, and the object to be measured is lighted by this radiation.

Detectors used in spectroscopic measurements comprise several detector elements connected to each other, each detector element measuring radiation coming from an object within different wavelength ranges. For a successful spectroscopic measurement, each detector element should see the object at the same incidence angle, in order that the multichannel detector formed by the detector elements may be used for measuring relative intensities of different wavelengths of the spectrum of the radiation reflected. In practice, it is, however, necessary to position the detector elements relatively far from each other for structural technical reasons, due to which the detector elements see the same object at slightly different angles or the radiation comes to the separate detector elements at the same angle, but has started from another part of the object than the radiation arrived at the rest of the detector elements. These problems appearing as error factors in measurements cannot be eliminated by fixed optics.

To eliminate these problems, it is known to use a diffuser in front of the detector elements. A parallel radiation bundle coming to the diffuser is diffused in the diffuser, which leads to that the radiation coming to the elements is mixed in different directions. On account of the operating principle of the diffuser, a large part of the radiation, i.e. of the light, passes the detectors, and the diffuser attenuates also the intensity of the radiation, because the more light rays come to the diffuser, the more the radiation is attenuated.

U.S. Pat. No. 4,792,684 discloses a horizontal scanner, which is used for instance in satellites or missiles to follow their movements. The device described in this publication directs the light rays collected by the device from several different directions and objects to one detector element. By this solution, it is not possible to avoid dimensional errors, because the light rays come from different places, due to which a ratio measurement taking place within a certain wavelength range would give somewhat erroneous measurement results. The mirror means to be used in the solution according to this publication comprises two separate levels, which are positioned at an angle with respect to each other. By means of this solution, it is not possible to circulate a focus on a detector level formed by several detectors. In this solution, moreover, the reflecting mirror is tilted to form a big angle of about 30° in relation to a level perpendicular to its rotating axis. The so-called split mirror structure causes a halving of the light intensity into two separate radiation beams.

U.S. Pat. No. 4,748,329 describes a method of and a system for measuring the thickness of a light transmitting film, whereby a multichannel detector measures radiation reflected from the surface. Several reflector means are used in this solution, by means of which the focus of radiation cannot be circulated by one mirror means on the same detector level over the separate detector elements.

German Patent 36 37 125 discloses a device for measuring reflection to be used in a spectrometer. In this device, reflection is measured at several different incidence angles and a corner prism included in the device returns the reflected light in the same direction, and then the light goes to a detector irrespective of a change in the incidence angle of the reflected radiation. By means of the simple device structure of the solution in question, it is not possible to provide a direction of radiation to a multi-channel detector in such a way that each detector element would see the radiation come to the detector elements at the same incidence angle with the same input aperture.

U.S. Pat. No. 4,923,263 discloses an optic scanner comprising two rotating mirrors tilted with respect to the rotating axis thereof, which scanner additionally comprises a field lens and a relaying transmission lens. The mirrors rotate at different speeds and at different phases, due to which several scanning figures of different shapes are obtained on the detector in the focal plane. This solution concerns a device with an operation similar to that of a camera, in which an image is produced on a first lens already and after that the image is transferred through mirrors to one and only detector. This solution does not show a focusing of a parallel radiation bundle as late as in the focal plane and an alternating circulation of the focus path created in this way over detector elements excited to different wavelengths, but a transfer of an image produced already earlier to the detector plane, i.e. to the focal plane. The dimensions of the image can be changed by means of a double-mirror structure.

U.S. Pat. No. 5,089,908 discloses an optic scanning system, by means of which a so-called plywood effect at image production shall be attenuated. The system comprises laser diodes at different wavelengths operating according to a control based on a video signal, the radiation of which diodes is directed through optics via a rotating polygon reflector over the detector plane. However, the structure of the rotating polygon reflector is in this solution such that it causes discontinuities in a light ray and losses in the radiation effect thereof, because the polygon reflector comprises numerous mirror surfaces, which, each in turn, reflect the radiation together with the rotating movement to the detector, whereby, when moving from one mirror surface to another, the radiation is interrupted and the focus of radiation returns to its starting point. This structure is suitable for image production for instance in copying machines, but not for spectroscopic applications. Also the basic structure of this system differs considerably from the present solution, for the system comprises several laser diodes operating at different wavelengths, and the system does not even comprise an object to be measured between the light source and the focusing optics and the rotating mirror.

Moreover, the publications WO 90/07697, U.S. Pat. Nos.

3,523,734, 4,687,329 and 5,050,991 disclose spectrometric methods and devices, in which radiation is deflected by means of a grid dispersing radiation, whereby the grid spreads the spot-like radiation to a line spectrum at the same time to the detectors, which is, however, no good solution in all applications.

Consequently, the solutions according to the prior art comprise a number of problems. The object of this invention is to set forth a novel method avoiding the problems associated with the known solutions.

SUMMARY OF THE INVENTION

This object is achieved by means of the method according to the invention, which is characterized in that the radiation coming from the object to be measured is directed by the optical means and the planar mirror means in such a way that, by rotating the mirror means tilted with respect to its axis round this axis and by keeping the radiation on the surface of the same planar mirror means, the focus of radiation is moved in a detector plane along a regular uninterrupted path alternatingly over each detector element positioned substantially in the same plane and excited at a different wavelength.

The method of the invention is based on the idea that the radiation coming from the same part of the object to be measured is brought at the same solid angle and with the same input aperture to the separate detector elements, without any substantial loss of radiation intensity, however.

Several advantages are achieved by the method of the invention. The elements of the detector see the object exactly at the same solid angle and at the same place, due to which the dimensional errors are eliminated. The device structure required for the realization of the method has a Good optical efficiency and is relatively simple and light and thus also safe to operate and durable, which is a special advantage in connection with portable measuring devices.

The invention also relates to a device for measuring optical radiation, which device comprises a means for lighting an object to be measured by substantially parallel radiation, an optic focusing means for directing the radiation coming from the object to be measured and a planar mirror means rotatable round its rotating axis for deflecting the radiation to be focused to a detector group comprising several detector elements. The device is characterized in that the optic focusing means directing radiation is arranged between the object to be measured and the planar mirror means in such a way and at such a distance from the mirror means that the radiation coming from the optic focusing means is focused during the whole measurement through the same plane surface of the planar mirror means at least approximately to the detector plane and that the planar mirror means between the optic focusing means and the detector group deflecting the radiation to be focused to the detector group is tilted to a small angle with respect to a plane rectangular to its rotating axis in such a way that the focus of the radiation can be moved by means of the mirror means rotatable round its rotating axis in a detector plane formed by the detector elements situated substantially in the same plane alternatingly over the separate detector elements.

The device according to the invention permits a radiation coming from the same part of the object to come at the same solid angle and with the same input aperture to all separate detector elements situated in the same detector plane. The optical efficiency of the device of the invention still remains sufficiently high. The device of the invention remains mechanically simple, which is a remarkable advantage in connection with portable measuring devices.

BRIEF DESCRIPTION OF THE DRAWINGS

The invention is described in the following in greater detail with reference to the enclosed drawings, in which.

DETAILED DESCRIPTION OF THE PREFERRED EMBODIMENTS

Figure 1:
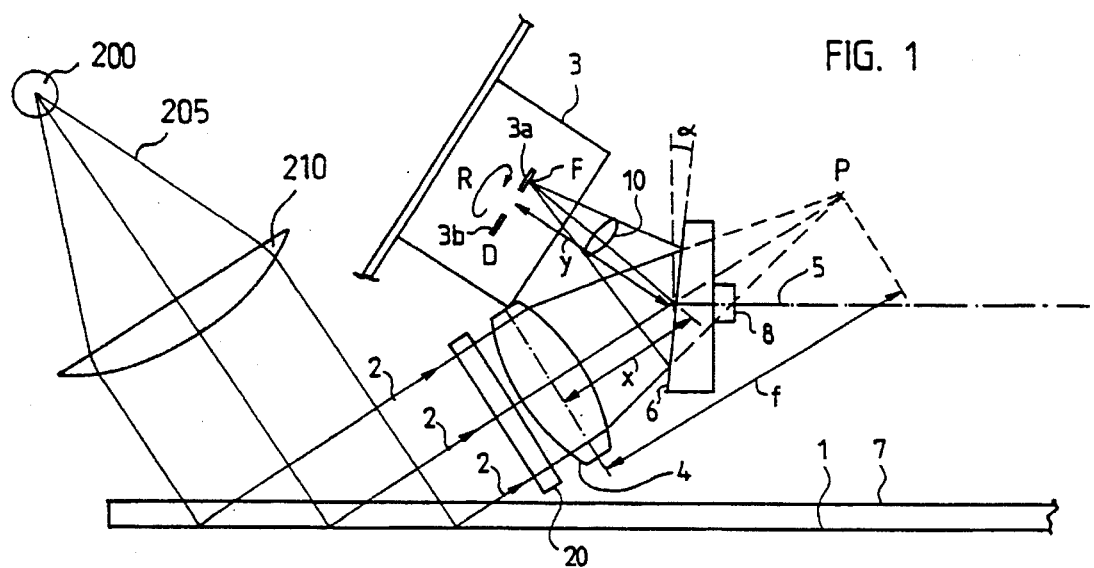
FIG. 1 shows general diagram of a device solution to be used in the method.
Figure 2:
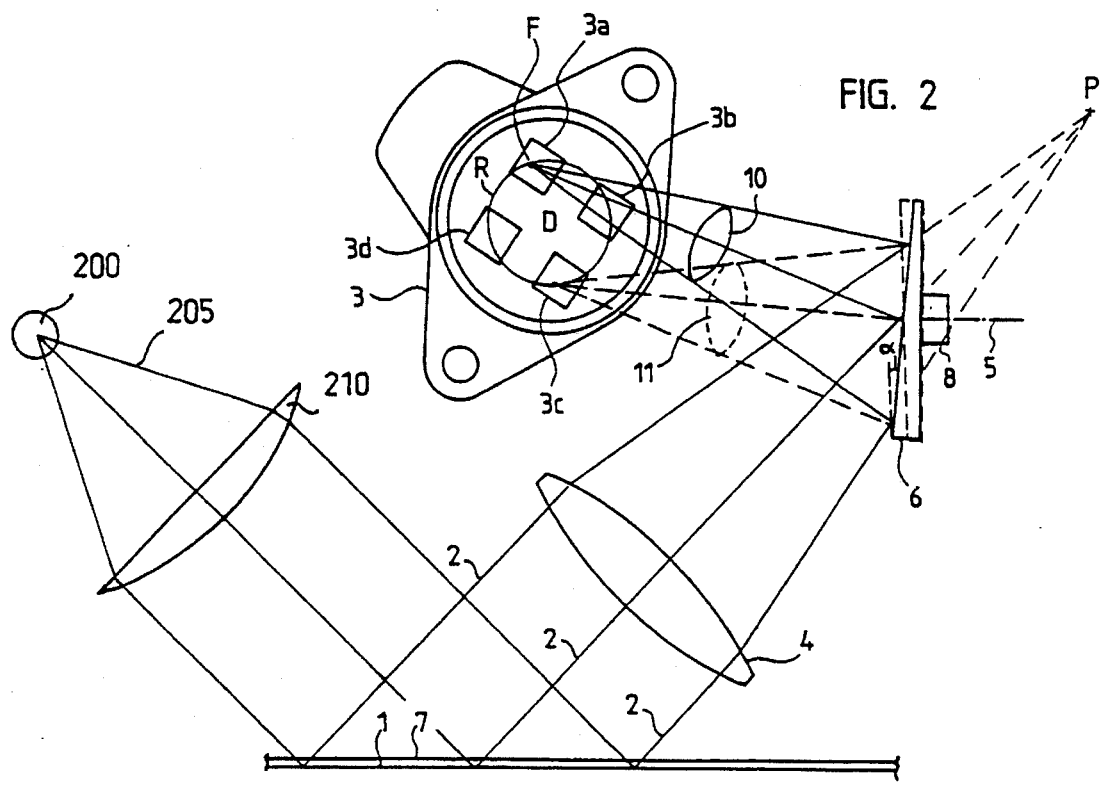
FIG. 2 shows the general diagram of the device solution to be used in the method seen towards a detector plane, FIG. 3 show a broadened path along which a focus rotated in detector plane circulates.

In FIGS. 1 and 2, a device solution according to the basic idea of the invention is used for instance in a spectrometric measurement for measuring an optical radiation 2 coming from an object 1 to be measured. The device comprises a multi-element detector group 3, i.e. a detector group comprising several detector elements 3a, 3b . . . , an optical means 4 for directing radiation and a mirror means 6 rotatable round its rotating axis 5 for deflecting radiation. The optical means 4 directing radiation can be used a convex lens, a lens combination, or a mirror. According to the inventive basic idea of the device solution, the optical means 4 directing optical radiation 2 is positioned between the object 1 to be measured and the mirror means 6 at such a distance from the mirror means 6 that the optical radiation 2 coming through the mirror means 6 to the detector group is focused through the mirror means 6 at least approximately in a detector plane D, and that the mirror means 6 between the optical means 4 and the detector group 3 is tilted to form a small angle α in relation to a plane perpendicular to its rotating axis 5 in such a way that a focus F of radiation can be moved in the detector plane D formed by the detector elements 3a to 3d situated substantially in the same plane over the separate detector elements 3a to 3d by means of the mirror means 6 rotatable round its rotating axis 5. On FIG. 2 can be commented that, for the sake of clarity, the detector group 3 and its detector plane D are shown slightly tilted backwards, in order that the movement of the focus F in the detector plane D could be seen more clearly.

The very focus P of the optical means 4, e.g. of a lens, is situated at the distance of a focal length f from the optical means 4. The optical means 4 is positioned at such a distance x from the mirror means 6 that the total of said distance x and a distance y between the detector plane D and the mirror means 6 is at least approximately equal to the focal length f of the optical means.

According to FIGS. 1 and 2, the optical radiation required for a measurement and to be directed to the object 1 to be measured and to a film 7 on its surface is provided either by means of an external light source 200 or a light source (not shown) included in the measuring device itself. The radiation 205 obtained from the spot-like light source 200 is made parallel, i.e. collimated, by a collimator lens 210.

In a preferred embodiment of the device, the mirror means 6 tilted to form a small angle α consists of a substantially integral aluminium piece, which makes the mirror means 6 light and advantageous and simple to manufacture. The lightness permits the mirror to be rotated by a small electric motor 8, the power consumption of which is only of the order below 4 mA. In a practical realization, the weight of the mirror means manufactured of aluminium was only about 3 grams. The machining properties of the mirror means of aluminium are relatively good.

Figure 3:
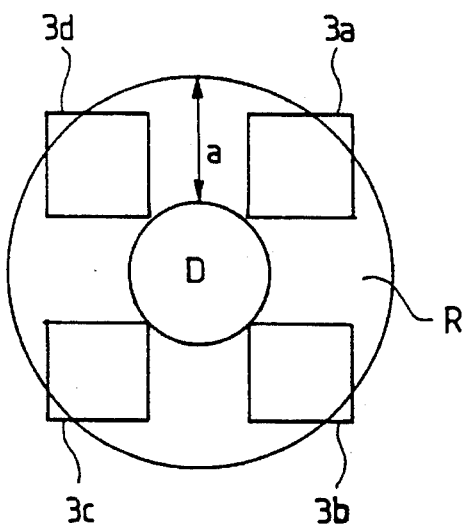
Figure 4:
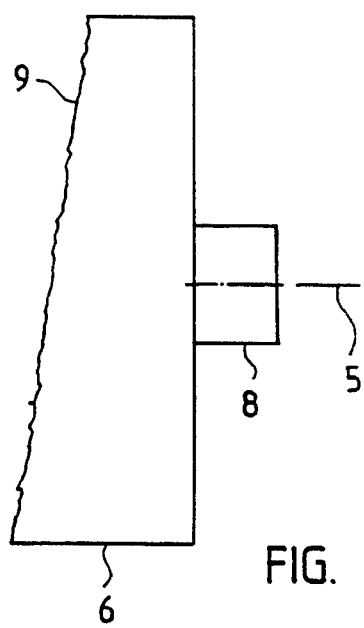
FIG. 4 shows a surface roughness formed on the surface of a mirror means.

In a preferred embodiment of the device of the invention, the device can additionally comprise a diffuser means consisting of a surface roughness 9 formed on the surface of the mirror means 6 according to FIG. 4. It has been possible to combine the diffuser means realized in this way with the rest of the device structure, i.e. in this case with the surface of the mirror means 6, in a compact manner. The above arrangement is very durable and usable, compared to the use of a diffuser lens 20. The surface of the mirror means 6 made of aluminium or some other material can be provided with the surface roughness 9 either as a separate stage of operation or by leaving the reflecting surface of the mirror means 6 slightly deficiently polished or possibly a little rough or dull. The diffuser means realized in this way, which in this case preferably means the surface roughness 9 of the mirror means of aluminium, provides a broadening of a path R, along which the focus circulates on the detector level D, to a breadth a or width "w" as shown in FIG. 3, which is thus much broader than the breadth of a thinner circular path R shown in FIG. 2. A diffuser means of this kind is needed, if there are surface defective areas or for instance dirt on the detector elements 3a to 3d. A broadened focus F attenuates the influence of such spotlike disturbances on the measurement result. FIG. 1 shows a diffuser, such as a diffuser plate 20, positioned directly on the optical path in front of the optical means 4, due to which the adjustability of the diffuser means can be implemented more easily.

In a preferred embodiment of the device solution, the tilt angle α of the mirror means with respect to a level perpendicular to the axis 5 thereof is smaller than 10°, preferably approximately 6°. Then the focus F can be circulated along the regular symmetric path R, but, however, at a sufficiently small incidence angle with respect to the detector plane D, in order that a use of interference filters (not shown) positioned in front of the detector elements 3a and 3b would be possible. The use of interference filters requires a sufficiently small incidence angle of radiation in relation to the detector plane D. Optical means of other kinds, such as polarizers, can also be used in front of the detectors.

The invention relates also to a method of measuring optical radiation 2 coming from an object 1 to be measured, for instance in a spectrometric measurement. Then by using the device solution according to the invention, the radiation 2 coming from the object 1 to be measured is measured in the method by focusing the radiation by an optical means 4 and a mirror means 6 on a detector group 3 comprising several detector elements. According to the basic idea of the method of the invention, the radiation 2 coming from the object 1 to be measured is directed by the optical means 4 to the mirror means 6, and a focus F of radiation is moved by rotating the mirror means 6 tilted with respect to its axis 5 round this axis 5 on a detector plane D along a regular path R over detector elements 3a to 3d positioned substantially in the same plane. Then the optical radiation coming from the object 1 to be measured is formed as a continuous radiation bundle, which is focused on the detector plane D. In a preferred embodiment of the method of the invention, the focus F is moved in the detector plane D over the detector elements 3a to 3d along a substantially circular, ellipsoidal or otherwise continuous path. Then the path of movement of the focus F is such that it can be focused on the detector plane D by means of a simple device solution. Referring to FIG. 3, if it were desirable to broaden the focus F of radiation for instance on account of impurities on the detector elements, then the focus F is broadened in the detector plane D by the aid of an integral diffuser means on the mirror means 6, which diffuser means is preferably a surface roughness 9 formed on the surface of the mirror means. In FIG. 3, the broadening of the focus is to be seen as an increase of a breadth "a" of the path R, along which the focus F circulates.

According to FIG. 2, the optical radiation to be focused by the optical means 4 is deflected by the mirror means 6 to the detector plane D, in which the focus F of the optical radiation is moved on the basis of the rotation of the mirror means 6 in turn over the separate detector elements 3a to 3d. FIG. 2 shows two conical bundles of radiation, i.e. radiation beams 10 and 11, tapering conically towards the detector, the latter one of which is indicated by broken lines. Respectively, two different positions are presented also for the mirror means, of which positions the one producing the beam 11 is also indicated by broken lines. The difference between the positions of the mirror means is 180°, i.e. the distance of half a turn round the axis 5 of the mirror means 6. The radiation beams 10 and 11 illustrate the focusing of a conically tapering radiation beam on the detector plane D at various moments of time. Thanks to the rotation of the mirror means 6 and the focusing influence of the optical means 4, e.g. a convex lens, the focus F of radiation can be moved easily in the same detector plane D over the separate detector elements 3a to 3d.

Figure 5:
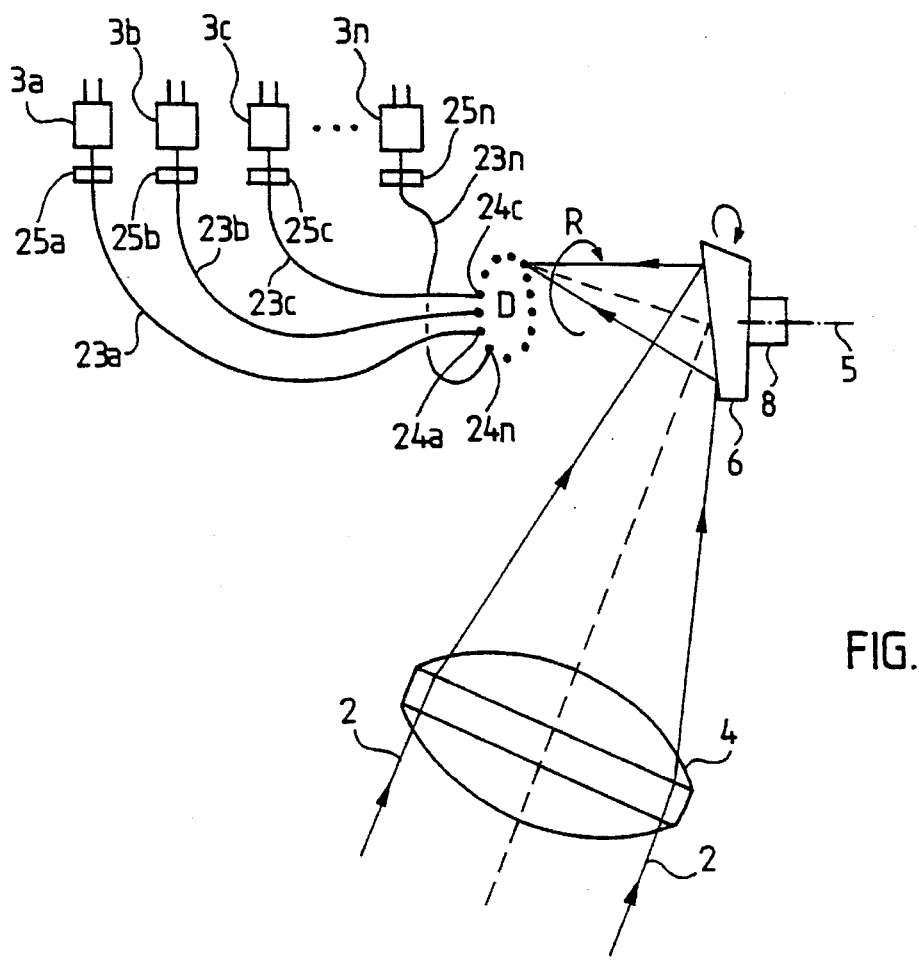
FIG. 5 shows another preferred embodiment of the device of the invention.

FIG. 5 shows another preferred embodiment of the device of the invention, in which fiber optic photoconductors 23a to 23n are connected to the actual detector elements 3a to 3n. Then in practice, the detector plane D will be a plane formed by ends 24a to 24n of the photoconductors 23a to 23n and the detector group 3 is formed by the actual detector elements 3a to 3n and the photoconductors 23a to 23n. As far as the terminology associated with detectors is concerned, the photoconductors 23a to 23n connected to the actual detector elements 3a to 3n shall be considered to be functionally included within the term "detector element". As a photoconductor can serve for instance an optical fibre or a bundle of optical fibres. By means of the solution of FIG. 5, the detector plane D itself can be made small in size, for the detector plane is formed by the ends 24a to 24n of the photoconductors 23a to 23n positioned in front of the detectors. By means of the structure of FIG. 5, it is possible to collect radiation to several optical fibres exactly at the same incidence angle, with the same aperture and from the same object. The fibre ends can be preferably positioned in a circular form according to the path R of the focus, whereby the collecting ratio of light is optimized.

In front of the detectors 3a to 3n, it is also possible to connect other means, such as wavelength filters, polarizers and other optical means, which are indicated in FIG. 5 by reference numerals 25a to 25n. The detector solution connected to photoconductors according to FIG. 5 is advantageous also in this case, for the additional other optical means 25a to 25n can be positioned between the actual detector elements 3a to 3n and the photoconductors 23a to 23n.

In FIG. 5, the measurement environment is presented in such a way that the figure shows no surface as an object to be measured from which light radiation would be reflected. On the contrary, it is a question of measuring the radiation 2 coming from an object to be measured, i.e. from a flue gas duct, for instance. Consequently, the method and the device according to the invention are suitable for measuring reflected radiation as well as radiation coming from the object in some other way.

Though the invention has been described above referring to the examples of the enclosed drawings, it is clear that the invention is not restricted to them, but it can be modified in many ways within the scope of the inventive idea presented in the enclosed claims.

We claim:

1. A method of spectroscopically measuring optical radiation, in which the intensity of radiation coming from an object (1) to be measured and exposed to collimated radiation is measured at a plurality of different wavelengths by focusing the radiation, via optical means (4) and mirror means (6), on a detector group (3) comprising a plurality of detector elements (3a to 3d), comprising the steps of:

a) orienting the optical means to direct the radiation to a planar surface of the mirror means, said planar surface being tilted at a small acute angle ($\alpha$) relative to a plane perpendicular to a rotational axis (5) of the mirror means, b) rotating the mirror means around said axis such that a focus (F) of the radiation moves in and defines a continuous, repetitious path (R) in a detection plane, and c) disposing the detector group with detection surfaces of the detector elements lying in said detection plane and in said path, such that the moving radiation focus repeatedly sweeps across the detection surfaces of the elements.

2. A method according to claim 1, wherein said path (R) is substantially circular or ellipsoidal.

3. A method according to claim 1, wherein the focus (F) is broadened in the detector plane (D) by integral diffuser means (9) on the mirror means (6).

4. A method according to claim 1, wherein the optical means comprises a focusing lens.

5. A device for spectroscopically measuring optical radiation, comprising:

a) means (200, 210) for lighting an object 1,7) to be measured with substantially parallel radiation, b) optical focusing means (4) for directing radiation (2) coming from the object to be measured, and c) planar mirror means (6) rotatable around an axis thereof for deflecting the radiation to a detector group (3) comprising a plurality of detector elements (3a to 3d), wherein d) the focusing means (4) is disposed between the object and the mirror means (6) such that the radiation coming from the optical focusing means is reflected by the planar surface of the mirror means and focused in a detection plane (D), e) the planar surface of the mirror means is tilted at a small acute angle ($\alpha$) with respect to a plane perpendicular to an axis (5) thereof, and f) the mirror means (6) is rotatable around said axis such that detection surfaces of the detector elements (3a to 3d) situated in the detection plane are repeatedly and sequentially swept by the focus (F) of the radiation moving in a continuous, repetitious path (R).

6. A device according to claim 5, wherein the mirror means (6) comprises a substantially integral aluminium member.

7. A device according to claim 5, further comprising diffuser means defined by roughness (9) formed on the surface of the mirror means.

8. A device according to claim 5, wherein the tilt angle ($\alpha$) of the mirror means surface is less than 10°, preferably approximately 6°.

9. A device according to claim 5, wherein said path (R) is substantially circular or ellipsoidal.

10. A device according to claim 5, wherein said detection surfaces of the detector elements are defined by ends (24a–24n) of fiber optic members.

* * * * *